United States Patent [19]

Abdallah et al.

[11] 3,934,020
[45] Jan. 20, 1976

[54] HALOPHENYL ACETAMIDINES AS ANXIOLYTIC ANTIDEPRESSANTS

[75] Inventors: Abdulmuniem H. Abdallah; Philip J. Shea, both of Midland, Mich.

[73] Assignee: The Dow Chemical Company, Midland, Mich.

[22] Filed: Oct. 2, 1974

[21] Appl. No.: 510,958

[52] U.S. Cl.......... 424/326; 260/501.14; 260/564 R
[51] Int. Cl............................................. A61k 31/155
[58] Field of Search..... 424/326; 260/564 R, 501.14

[56] References Cited
UNITED STATES PATENTS
3,445,517  5/1969  Mills .................................. 424/326

OTHER PUBLICATIONS

Chem. Abst., 71-111086(t) (1969).
Chem. Abst., 71-123763(z) (1969).
Chem. Abst., 65-2182(d) (1966).

Primary Examiner—Stanley J. Friedman
Attorney, Agent, or Firm—Maynard R. Johnson

[57] ABSTRACT

A method useful for alleviating central nervous system depression and anxiety symptoms comprises administration to animals of an effective amount of an N,N'-dialkyl-2-halophenyl acetamidine. Compositions useful in practicing the method are also disclosed.

7 Claims, No Drawings

HALOPHENYL ACETAMIDINES AS ANXIOLYTIC ANTIDEPRESSANTS

CROSS-REFERENCE TO RELATED APPLICATION

The compounds employed in the method and composition of the invention can be prepared in procedures described in a copending, commonly-assigned application by James R. McCarthy, Jr., Ser. No. 510,955, filed concurrently herewith.

BACKGROUND OF THE INVENTION

Description of the Prior Art

The substituted amidine compounds of the invention can be prepared by a modification of known methods. Typical methods which can be so modified include the reaction of a nitrile with a trialkyloxonium fluoroborate to prepare an N-alkyl nitrilium salt and reaction of the salt with a primary amine similar to that of Meerwein et al., Ber. 89, 209 (1956), Borch, J. Org. Chem., 34, 627 (1969), and Weintraub et al., J. Org. Chem. 33, 1679 (1968). A number of N-monosubstituted and unsubstituted amidines are known. Craver et al., J. Pharm. Exptl. Therap. 99, 353 (1950); Netherlands Application No. 6,508,754, C.A. 65, 2181c (1966); U.S. Pat. Nos. 3,344,138, 3,417,122 and 3,334,137. Chlorobenzamidines are disclosed by Markwardt et al., Pharmazie 1969 24 (7), 400–2, and European J. Biochem. 6; 502–6(1968).

SUMMARY OF THE INVENTION

This invention is directed to a method which comprises administering to a mammal an effective antidepressant or anxiolytic amount of substituted halophenyl acetamidine compound or a pharmacologically-acceptable salt thereof, or a composition containing such substituted acetamidine compound or salt as the active antidepressant-anxiolytic ingredient therein; said substituted halophenyl acetamidine compound corresponding to the formula:

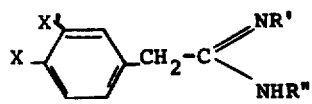

wherein X and X' each independently represent halo, trifluoromethyl or hydrogen with the proviso that at least one of X and X' is halo or trifluoromethyl; and R' and R" each independently represent a loweralkyl substituent of one, two or three carbon atoms. In the present specification and claims "halo" refers to chloro and bromo.

It has been found that the 2-halophenyl acetamidines of the above formula and their pharmacologically-acceptable salts have potent antidepressant and anxiolytic properties. (For the purpose of brevity, such compounds will be hereinafter referred to as "substituted amidines".) Administration of one or more of the substituted amidine compounds to mammals has been found to provide valuable antidepressant effects accompanied by anxiolytic or calming effects, thus providing for alleviation of central nervous system depression without accompanying central nervous stimulation or agitation; and in a corresponding manner, providing alleviation of symptoms of anxiety or nervous agitation without accompanying central nervous system depressant effects. The compounds have exhibited little or no significant detrimental pharmacological effects at dosages consistent with good antidepressant-anxiolytic activity.

The substituted amidine compounds are crystalline solids which are soluble in a variety of conventional liquids, including alcohols, chlorinated hydrocarbons, etc. In general, the pharmacologically-acceptable salts and more soluble in aqueous liquids than are the free base compounds, and the substituted amidines are preferably employed in the form of such salts.

As employed herein, the phrase "pharmacologically-acceptable salt" refers to salts of the substituted amidines, the anions of which are relatively non-toxic and innocuous to mammals at dosages consistent with good activity so that side effects ascribable to the anions do not vitiate the beneficial effects of the substituted amidines. suitable pharmacologically-acceptable salts which can be employed in the method and composition of the invention include those derived from mineral acids such as the hydrochloride, hydrobromide, phosphate, nitrate and sulfate salts, those derived from organic carboxylic acids such as the succinate, tartrate, citrate, malate, maleate, and acetate salts and those derived from organic sulfonic acids such as the methanesulfonate and toluenesulfonate salts.

In practicing the method, one or more substituted amidine is administered internally to a mammal by a route effective to introduce an effective amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood stream via the gastrointestinal tract. The substituted amines are orally effective, and generally have a higher ratio of toxic dose to effective dose when orally administered, and this route is preferred.

The effective amount of substituted amidine to be administered can also be referred to as an "antidepressant amount" (amount sufficient to alleviate central nervous system depression); as an "anxiolytic amount" (amount sufficient to alleviate symptons of anxiety, i.e., symptoms of central nervous system agitation; or as an "antidepressant-anxiolytic amount", since the dosage sufficient to provide antidepressant effect also provides some anxiolytic effect, and vice-versa. In the present specification, the terms can be regarded as interchangeable with respect to dose.

The antidepressant-anxiolytic amount of compound, that is, the amount of the substituted amidine compound sufficient to provide the desired effect depends on various known factors such as the size, type, age and condition of the animal to be treated, the particular amidine or pharmacologically-acceptable salt employed, the route and frequency of administration, the type and degree of central nervous system condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at dosage rates from about 1 to about 4 to about 25 to about 50 milligrams of substituted amidine compounds per kilogram of animal body weight. Higher dosage rates may be employed, for example, when the compound is administered orally in a timed release dosage form. When administered by injection, good results are obtained with an amount of from about 1 to about 25 milligrams of the amidine compound per kilogram of animal body weight. From about 1 to 120 milligrams of the amidine compound per kilogram, depending on dosage unit form employed, provide good results when the compound is administered orally. In the case of mammals suffering from central nervous system depression or exhibiting symptoms of anxiety, administration of an antidepressant-anxiolytic amount of the substituted amidine compound is preferably repeated at predetermined intervals. It is generally desirable to administer the individual dosages at the lowest antidepressant-anxiolytic amount which provides the desired continuity consonant with a convenient dosing schedule. In a convenient repetitive procedure, the substituted amidines are administered in single or divided oral doses at daily rates of about 1 to 150 milligrams per kilogram per day.

In practicing the method of the invention, the active ingredient is preferably incorporated in a composition comprising a pharmaceutical carrier and from about 0.001 to about 95 percent by weight of the substituted amidine compound of a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa.(1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active amidine compound can be formulated in conventional timed release capsule or tablet formulations.

Preferred compositions include sterile injectable solutions containing from about 0.001 to about 10 percent by weight of the amidine compound in a pharmaceutical carrier suitable for injection, such as isotonic saline solution, Ringer's Injection USP, and lactated Ringer's USP, and the like. Preferred compositions for oral use include unit dosage forms such as capsules and compressed tablets, containing a pharmaceutical carrier and from about 1 to about 150 milligrams of amidine compound per unit.

The following examples are illustrative of the invention.

EXAMPLE 1

Separate groups of mice of the same origin and past history (5 mice per group) were administered N,N'-dimethyl-2-(4-chlorophenyl) acetamidine hydrochloride as a solution in saline. Different groups were administered the compound by intraperitoneal injection at various dosage rates. Thirty minutes after the administration of the test compound, the mice were administered reserpine at a dosage rate of 2.5 milligrams per kilogram by intraperitoneal injection. Separate groups of similar mice were similarly administered 2.5 milligrams of reserpine per kilogram 30 minutes after administration of various dosages of the known antidepressant. The mice were then observed for 45 minutes for symptoms of reserpine-induced depression.

In repeated prior check observations, the administration of 2.5 milligrams per kilogram (mg/kg) of reserpine intraperitoneally to mice has been observed to result in a classical progression of symptoms beginning with a characteristic dropping of the eyelids (ptosis) and later culminating in a generalized depression with decreased spontaneous motor activity and decreased responsiveness to auditory and tactile stimuli. Protection from reserpine-induced depression is indicated by the absence of the characteristic ptosis.

The results were employed to calculate the dose effective to protect 50 percent of the mice ($ED_{50}$) by classical statistical procedures. The amidine compound was found to have an $ED_{50}$ of 2 mg/kg. In other operations the intraperitoneal acute 50 percent lethal dose ($LD_{50}$) was found to be 69 mg/kg.

EXAMPLE 2

The procedure of Example 1 was repeated, using oral administration of N,N'-dimethyl-2-(4-chlorophenyl) acetamidine hydrochloride instead of intraperitoneal injection. The oral $ED_{50}$ was found to be 3 mg/kg. The oral $LD_{50}$ was found to be 430 mg/kg.

In a similar operation carried out with rats as the test animals, the oral $ED_{50}$ of the same compound was found to be 2 mg/kg.

In similar operations carried out with N,N'-diethyl-2-(3,4-dichlorophenyl)acetamidene hydrochloride, the intraperitoneal and oral $ED_{50}$'s were found to be 9 and 13 mg/kg, respectively.

EXAMPLE 3

Calmative or anxiolytic effect is evaluated in a procedure similar to the electric shock induced aggression procedure of Tedeschi et al., J. Pharm. Exptl. Therap. 125, 28–34 (1959). Aggression and fighting were induced in pairs of mice by mild foot shock (3 milliamperes, 0.2 seconds duration, 3 shocks per second) applied to a cage floor grid over a 2 minute period. The number of fighting episodes was counted during the 2 minute period, and aggression recorded as present or absent if fighting episodes are more or less than the mean number of episodes, plus or minus 1.5 standard deviations, obtained with mice administered only saline solution. In this procedure, N,N'-dimethyl-2-(4-chlorophenyl) acetamidene hydrochloride, administered by intraperitoneal injection in sterile saline solution, is found to inhibit aggression with an $ED_{50}$ of 43 milligrams per kilogram. The known anti-anxiety (anxiolytic) agents diazepam, chlordiazepoxide and chlorazepate dipotassium also inhibit aggression in this procedure with i.p. $ED_{50}$'s between 4 and 30 mg/kg.

EXAMPLE 4

In other operations with the test compound, N,N'-dimethyl-2-(4-chlorophenyl)acetamidine hydrochloride, a number of other pharmacological evaluations are carried out.

The test compound is found to have no effect on pentylenetetrazole induced convulsions at i.p. dosages up to 46.4 mg/kg and no effect on tryptamine induced convulsions in rats.

The test compound is found to have no significant effect on behavior of mice trained to avoid electric shock administered via a cage floor grid by jumping to a platform, at i.p. dosages of 10, 21.5 and 46.4 mg/kg.

The test compound is found to potentiate symptoms of hyperexcitability, fighting and death induced by subcutaneous injection of 20 mg/kg of yohimbine hydrochloride in aggregated mice, with an $ED_{50}$ of 15 mg/kg (i.p.) when administered 30 minutes prior to yohimbine challenge.

What is claimed is:

1. A method useful for alleviating symptoms of central nervous system depression and anxiety in an animal comprising administering to an animal an amount of a compound selected from the group consisting of a substituted amidine and a pharmacologically-acceptable salt thereof effective to alleviate said symptoms, the substituted amidine corresponding to the formula:

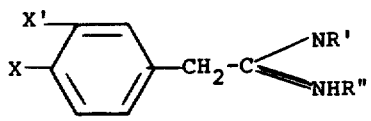

wherein X and X' each independently represent halo, trifluoromethyl or hydrogen, with the proviso that at least one of X and X' is halo or trifluoromethyl and R' and R'' each independently represent loweralkyl.

2. Method of claim 1 where R' and R'' both represent methyl.

3. Method of claim 2 wherein the compound is N,N'-dimethyl-2-(4-chlorophenyl)acetamidine hydrochloride.

4. A method useful for alleviating symptoms of central nervous system depression in a mammal comprising administering to a mammal suffering from central nervous system depression an amount of a compound selected from a substituted amidine and a pharmacologically-acceptable salt thereof effective to alleviate said symptoms, the substituted amidine corresponding to the formula:

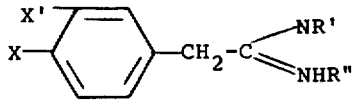

wherein X and X' each independently represent halo, trifluoromethyl or hydrogen, with the proviso that at least one of X and X' is halo or trifluoromethyl and R' and R'' each independently represent loweralkyl.

5. Method of claim 4 where R' and R'' both represent methyl, and X and X' both represent chloro.

6. A method useful for alleviating symptoms of anxiety in a mammal comprising administering to a mammal exhibiting symptoms of anxiety an amount of a compound selected from the group consisting of a substituted amidine and a pharmacologically-acceptable salt thereof effective to alleviate said symptoms, the substituted amidine corresponding to the formula:

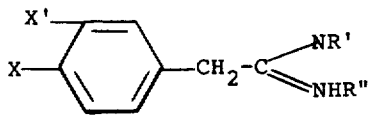

wherein X and X' each independently represent halo, trifluoromethyl or hydrogen, with the proviso that at least one of X and X' is halo or trifluoromethyl and R' and R'' each independently represent loweralkyl.

7. Method of claim 6 where R' and R'' both represent methyl, and X and X' both represent chloro.

* * * * *

UNITED STATES PATENT AND TRADEMARK OFFICE
CERTIFICATE OF CORRECTION

PATENT NO. : 3,934,020
DATED : January 20, 1976
INVENTOR(S) : Abdulmuniem H. Abdullah and Philip J. Shea It is certified that error appears in the above-identified patent and that said Letters Patent are hereby corrected as shown below:

Column 2, line 9, first word "and" should read -- are --.

Column 2, line 44, "symptons" should read -- symptoms --.

Column 3, line 26, "compound of" should read -- compound or --.

Column 4, line 58, a comma "," was omitted following the word procedure.

Signed and Sealed this

Fourth Day of January 1977

[SEAL]

Attest:

RUTH C. MASON
*Attesting Officer*

C. MARSHALL DANN
*Commissioner of Patents and Trademarks*